United States Patent [19]

Janssens et al.

[11] 3,932,418

[45] Jan. 13, 1976

[54] ELECTROPHOTOGRAPHIC MATERIAL

[75] Inventors: Wilhelmus Janssens, Aarschot; Johannes Josephus Vanheertum, Halle-Zandhoven; Robert Joseph Pollett, Vremde; Hendrik Hubert Sneyers, Wijnegem; Jozef Aime Dierckx, Mechelen, all of Belgium

[73] Assignee: AGFA-GEVAERT N.V., Mortsel, Belgium

[22] Filed: Oct. 18, 1973

[21] Appl. No.: 407,650

Related U.S. Application Data

[62] Division of Ser. No. 304,939, Nov. 9, 1972, Pat. No. 3,798,031.

[30] Foreign Application Priority Data

Nov. 10, 1971 United Kingdom .............. 52287/71

[52] U.S. Cl. ......... 260/288 CE; 96/1.8; 260/240 R; 260/240 F; 260/240.1; 260/240.7; 260/243; 260/244; 260/283 CF; 260/283 PF; 260/283 T; 260/283 BY; 260/283 S; 260/288 CF; 260/289 C; 260/293.57; 260/293.58; 260/293.61; 260/293.62; 260/296 N

[51] Int. Cl.² ........................................ C07D 215/12

[58] Field of Search .................... 260/288 R, 283 BI

[56] References Cited

UNITED STATES PATENTS

| | | | |
|---|---|---|---|
| 2,791,588 | 5/1957 | Collier et al. | 260/283 BI |
| 3,152,134 | 10/1964 | Humber | 260/283 BI |
| 3,491,099 | 1/1970 | Copp | 260/288 R |

OTHER PUBLICATIONS

Buchmann et al.; *Chem. Abstracts, Vol. 58, p. 3392–3393; 1963.*

Mndyhoyan et al.; Chem. Abstract; Vol. 59; p. 6362*a*, 1963.

Fernandez et al.; Chem. Abst., Vol. 64, p. 6612, 1966.

*Primary Examiner*—Donald G. Daus
*Assistant Examiner*—Mary C. Vaughn
*Attorney, Agent, or Firm*—William J. Daniel

[57] ABSTRACT

Electrophotographical recording process wherein a pattern of increased conductivity is produced image-wise in a photoconductive insulating recording layer containing as essential photoconductive compound a photoconductive 1,2,3,4-tetrahydroquinoline. The photoconductive compound can be chemically and spectrally sensitized and charged either negatively or positively.

2 Claims, No Drawings

ELECTROPHOTOGRAPHIC MATERIAL

This is a division of Ser. No. 304,939 filed Nov. 9, 1972, now U.S. Pat. No. 3,798,031.

This invention relates to recording and reproduction of information-wise modulated electromagnetic radiation and to recording materials suitable therefor, particularly to such processes and recording materials containing one or more organic photoconductive compounds as hereinafter described.

It has now been found that a particularly photosensitive photoconductive recording member can be formed by using in its composition a photoconductive compound corresponding to the following general formula (I):

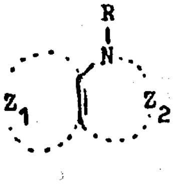

wherein:

$Z_1$ represents the necessary atoms to close an adjacent aromatic nucleus or an adjacent aromatic ring system including an adjacent aromatic nucleus or aromatic ring system substituted with (a) non-ionic substituent(s) e.g. substituted with an alkyl group for example methyl, halogen e.g. F, Cl, Br or I, an alkoxy group e.g. methoxy, an amino group, a substituted amino group e.g. a monoalkylamino or dialkylamino group or a cyano group, $Z_2$ represents the necessary methylene groups or substituted methylene groups to close a 6-membered heterocyclic nitrogen-containing nucleus. Suitable substituents for the methylene groups are one or more $C_1$–$C_4$ alkyl groups e.g. methyl, and R represents hydrogen, an aliphatic radical including a saturated aliphatic radical, an unsaturated aliphatic radical, a cyclo-aliphatic radical and these radicals in substituted form, or an alkylene group which is ring-closed with the carbon atom in peri-position of the aromatic ring closed by $Z_1$ in order to form a julolidine compound.

According to a preferred embodiment R represents an organic group that can be introduced by alkylation, for example an alkyl radical including a substituted alkyl radical e.g. methyl a cycloalkyl radical, e.g. cyclohexyl, an allyl radical, an aralkyl radical, e.g. benzyl.

The adjacent aromatic nucleus or ring system closed by the atoms represented by $Z_1$ is preferably one of the unsubstituted or substituted nuclei or ring systems represented by the following structural formulae:

(benzene)

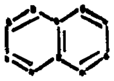

(naphthalene)

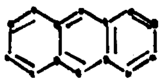

(anthracene)

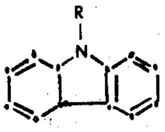

(carbazole)

wherein R represents hydrogen or an alkyl group e.g. methyl or ethyl

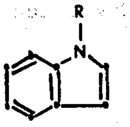

(indole)

wherein R represents hydrogen or an alkyl group e.g. methyl or ethyl.

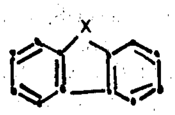

(dibenzofuran)
(dibenzothiophene)

wherein: X represents oxygen or sulphur

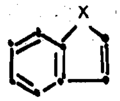

(benzofuran)
(benzothiophene)

wherein: X represents oxygen or sulphur

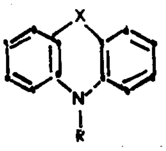

(phenothiazine)
(phenoxazine)

wherein:

X represents oxygen or sulphur, and

R represents hydrogen or an alkyl group e.g. methyl or ethyl.

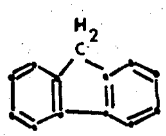

(fluorene)

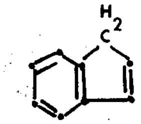

(indene)

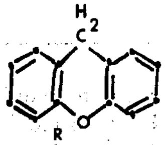

(xanthene)

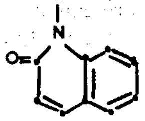

(quinolin-2-one)

wherein: R is hydrogen or an alkyl group e.g. methyl or ethyl.

Preferred photoconductive compounds according to the present invention and which are considered as new compounds are within the scope of the following general formula (II):

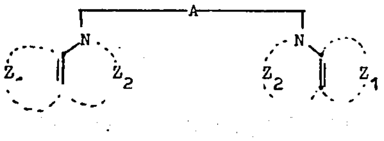

wherein:

$Z_1$ and $Z_2$ have the same significance as described in the above general formula, and A represents a bivalent organic radical of the type that can be introduced by alkylation, e.g. A represents an alkylene group, a substituted alkylene group or an alkylene chain interrupted by a bivalent aromatic group. Preferably A represents $-CH_2-CH_2-$ or

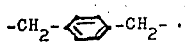

Particular examples of photoconductive compounds according to the general formula (I) are listed in the following Table I.

Table I

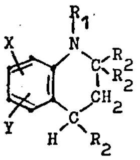

| No. | $R_1$ | $R_2$ | X | Y | Melting or boiling point |
|---|---|---|---|---|---|
| 1 | 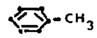 | $CH_3$ | 6—$CH_3$ | 7—$CH_3$ | oily product |
| 2 | H | $CH_3$ | 6—$CH_3$ | 7—$CH_3$ | oily product 105–106°C/0.5 mm Hg |
| 3 | $CH_3$ | $CH_3$ | H | H | 98–100°C/1 mm Hg oily product |
| 4 | $CH_3$ | H | H | H | oily product 130–132°C/15 mm Hg |
| 5 | | H | H | H | 145–149°C/0.2 mm Hg |
| 6 | H | $CH_3$ | 6—$C_2H_5O$ | H | 148–151°C/3 mm Hg |
| 7 | (1)—$CH_2$—$CH_2$—$CH_2$—(8) (julolidine) | H | (8)—$CH_2$—$CH_2$—$CH_2$—(1) | H | oily product 105–109°C/1 mm Hg |
| 8 | 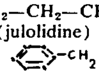 | $CH_3$ | 6—$C_2H_5$—O— | H | 86°C |
| 9 | 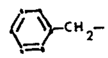 | $CH_3$ | 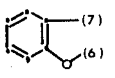 | | 138°C |
| 10 | H | $CH_3$ | 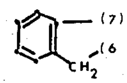 | | 116°C |

Particularly useful photoconductive compounds according to the general formula (II) are listed in the following Table II. These compounds are called "duplo compounds" for they include two 1,2,3,4-tetrahydroquinoline nuclei.

Table II

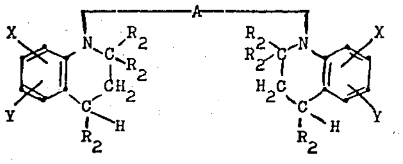

| No. | $R_2$ | A | X | Y | Melting point °C |
|---|---|---|---|---|---|
| 1 | $CH_3$ | $(CH_2)_2$ | H | H | 107 |
| 2 | H | $(CH_2)_2$ | H | H | 151 |
| 3 | $CH_3$ | $(CH_2)_2$ | 6—$C_2H_5O$ | H | 127 |
| 4 | $CH_3$ | $(CH_2)_2$ | 6—$CH_3$ | H | 179 |
| 5 | $CH_3$ | $(CH_2)_2$ | 6—$CH_3$ | 7—$CH_3$ | 172 |
| 6 | H | 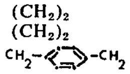 | H | H | 124 |
| 7 | $CH_3$ | 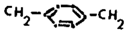 | H | H | 163 |

The preparation of the compounds according to the formula of Table I proceeds by hydrogenation of the corresponding 1,2-di-hydroquinoline compounds which are prepared e.g. according to a procedure described in the Belgian Pat. Nos. 775,786 filed Nov. 25, 1971 and 776,380 filed Dec. 8, 1971 both by Agfa-Gevaert N.V.

The substitution of the hydrogen atom in the NH group of the $Z_2$-ring by an organic group may proceed according to known alkylating techniques. This alkylation may be carried out before or after the hydrogenation of the double bond between the 3- and 4-carbon atom in the 1,2-dihydroquinoline compound.

For introducing an alkyl substituent by substitution of the hydrogen atom of said NH group any suitable alkylating agent e.g. trialkyl phosphate, alkyl iodides, alkyl bromides and alkyl chlorides may be used, the latter preferably in conjunction with a small amount of potassium iodide.

The preparation of the "duplo-compounds" as e.g. represented in Table II proceeds by linking together two 1,2,3,4-tetrahydro-quinolines by alkylation through the nitrogen atoms in the 1-position.

As suitable bifunctional alkylating agents are to be mentioned dihalogenated reactants of the formula Hal-A-Hal in which Hal represents a replaceable halogen atom e.g. chlorine, bromine or iodine and A has the same significance as described above.

The following are illustrative of reactants that may be used in the preparation of the duplo-compounds:

ethylene dichloride, dibromide and diiodide
1-chloro-2-bromoethane
propylene dichloride, dibromide and diiodide
trimethylene dichloride, dibromide and bromoiodide
butylene dichloride, dibromide and diiodide
tetramethylene dichloride, dibromide and diiodide
pentylene dichloride, dibromide and diiodide
hexamethylene dichloride dibromide and diiodide
hexylene dichloride, dibromide and diiodide
octylene dichloride, dibromide and diiodide
pentamethylene dichloride, dibromide and diiodide
alpha, beta-styrene dichloride, dibromide and diiodide
1,2-dibromocyclohexane
1,3-dibromobutane
1,2-dibromobutane
1,4-dichlorobutene-2
2-phenyl-1,2-dibromopropane
1-p-tolyl-1,2-dichloroethane
1,4-di(chloromethyl)benzene
1,4-di(bromoethyl)benzene
1,4-di(iodomethyl)benzene
1-(2,4-dichlorophenyl)-1,2-dichloroethane
1-(p-chlorophenyl)-1,2-dibromoethane
decamethylene dichloride, dibromide and diiodide
dodecamethylene dichloride, dibromide and diiodide
1,2-dibromobutene-3
1,2-dichloropentene-4
1,2-dichloro-3-methylbutene-3
1,4-dichlorobutene-2
1,4-dibromo-2,3-dimethylbutene-2
1,2-dichlorocyclopentene-3
1,4-dibromocyclopentene-2
1,4-dibromo-2,6-dimethylheptene-2
2,3-dichloro-2,6-dimethyloctene-6

Other suitable reactants for the duplo-compound formation are the $\beta$-chloroethyl ester of p-tolusulphonic acid and the p-tolusulphonic acid glycol diester.

Preferred reactants are sym.-dibromoethane and sym.-dichloroethane.

The acid produced during the alkylation reaction may be neutralized by any alkaline neutralizing agent ordinarily employed for neutralizing acids produced in condensation reactions e.g. an organic base.

The following preparations illustrate in more details the manufacture of the compounds enumerated in the Tables I and II.

PREPARATION OF COMPOUND 5 OF TABLE I 0.1 mole of the corresponding 1,2,3,4-tetrahydroquinoline was mixed with 0.3 mole of benzyl chloride in the presence of 0.12 mole of anhydrous sodium carbonate in 150 ml of ethanol. The reaction mixture was refluxed for 6 h whereupon it was filtered. The solvent was removed from the filtrate by evaporation. The residue was washed with cold methanol and distilled under reduced pressure. The fraction boiling between 145°C and 149°C at 0.2 mm Hg was collected.

Compound 1 of Table I was prepared analogously. Compounds 8 and 9 were recrystallized from acetonitrile.

PREPARATION OF COMPOUND 2 OF TABLE I 0.2 Mole of the corresponding 1,2-dihydroquinoline and 4 ml of a dispersion of Raney nickel were mixed with 150 ml of dioxan. Hydrogen pressure of 1500 psi was applied and the hydrogenation effected at 70°C for 2 h. The measured hydrogen acception corresponded with the theoretically possible value. After removal by filtering of the Raney nickel the solvent was removed by evaporation and the residue distilled under reduced pressure with the help of a fractionating column. The fraction boiling between 105°–106°C at 0.5 mm Hg was collected.

Compounds 3 and 10 of Table I were prepared analogously.

Compound 10 was not distilled but recrystallized from ligroin in the presence of active carbon.

PREPARATION OF COMPOUND 4 OF TABLE I

A mixture of 0.2 mole of 1,2,3,4-tetrahydroquinoline, 0.4 mole of trimethyl phosphate and 0.21 mole of ethyl diisopropylamine were heated at 140°C on an oil-nath for 1 n.

The reaction mixture was poured into water and treated with sufficient ammonium hydroxide for obtaining a slightly alkaline reaction.

The obtained supernatant oily product was extracted with chloroform. The whole mixture was washed with 2N aqueous hydrochloric acid and thereupon washed with water until neutral. After drying on anhydrous sodium sulphate the extract was distilled under reduced pressure with a distillation column and the fraction boiling between 130°–132°C at 15 mm Hg collected.

PREPARATION OF COMPOUND 6 OF TABLE I 90.5 g of the corresponding 1,2-dihydroquinoline were hydrogenated in the presence of Raney nickel under 1500 psi of hydrogen pressure at 70°C in dioxan as a solvent. After removal of the Raney nickel by filtering the solvent was evaporated under reduced pressure and the hydrogenated product purified by distillation. The fraction boiling between 148°–151°C at 3 mm Hg was collected.

PREPARATION OF COMPOUNDS 1,3,4 AND 5 OF TABLE II

The hydrogenation of the corresponding 1,2-dihydroquinoline to the indicated 1,2,3,4-tetrahydroquinoline of Table II proceeded in a total liquid volume of 300 ml by using 0.1 mole of the 1,2-dihydroquinoline, 3 ml of Raney nickel dispersion and the balance of dioxan at 1500 psi. The hydrogenation was effected at 85°C for 2 h. The hydrogen acceptance was slightly more than the theoretical value. After removal of the Raney nickel by filtering the solvent was evaporated.

Compound 1 was recrystallized from acetonitrile, compound 3 from butanol and compounds 4 and 5 from ethanol.

PREPARATION OF COMPOUND 2 OF TABLE II

The alkylation was carried out by heating with stirring 0.2 mole of the 1,2,3,4-tetrahydroquinoline with 0.1 mole of sym.-dibromoethane and 0.2 mole of triisopropanolamine at 100°C for 10 h. The obtained reaction product was extracted with dichloroethane and washed first with 2N aqueous hydrogen chloride and then with water until neutral.

The extract was dried over anhydrous sodium sulphate and after filtering the solvent was removed. Recrystallization of the crude product from ethylene glycol monomethyl ether yielded a white powder.

Melting point: 151°C. Yield: 54%.

In the preparation of the compounds 6 and 7 of Table II 1,4-di(monochloromethyl)benzene was used instead of sym.dibromoethane.

The photoconductive duplo compounds of Table II are particularly interesting for their high photosensitivity and pure state wherein they can be separated. Most of these products are obtained as white powders, which are suited for producing very clear colourless photosensitive layers.

The photoconductive compounds applied according to the present invention may be used alone or in combination with substances imparting desired chemical or physical properties to the recording element. So, these substances may be combined with other substances that either or not are photoconductive and exert an influence e.g. on the dark-resistivity, the dischargeability or conductivity of the recording layer by an exposure to electromagnetic radiation, or on the transparency or the quality of the final image, e.g. by counteracting the fringe effect as described in the United Kingdom Pat. No. 1,007,349 filed Oct. 12, 1961 by Gevaert Photo-Producten, N.V.

A proper combination with selected binding agents and/or chemical sensitizing agents may result in an enhancement of the total sensitivity. The recording elements according to the present invention preferably contain at least 5% by weight of a photoconductive 1,2,3,4-tetrahydroquinoline derivative being within the scope of the above general formulae. For use in electrophotography the recording element preferably consists for at least 10% by weight of one or more of the said 1,2,3,4-tetrahydroquinoline derivatives. The electrically insulating binding agent used in a recording layer containing said derivative may provide the desired mechanical strength for instance to form a self-supporting layer, and preferably has a resistivity of at least $10^9$ ohm.cm.

According to a particular embodiment the recording layer consists of the photoconductor, which, e.g., has been applied to a suitable support in molten state forming a micro-crystalline or glass-like layer on cooling. This technique can be applied when the photoconductive recording element has not to possess a high mechanical strength. For such technique reference is made to the Canadian Pat. No. 712,541 filed Feb. 5, 1960 by Gevaert Photo-Producten N.V.

Macromolecular compounds suitable for use as insulating binding agent for the photo-conductive compounds are, e.g., natural resins such as dammar resin, gum arabic, microcrystalline waxes, modified natural substances such as cellulose diacetate, cellulose triacetate, and ethylcellulose, pentaerythrite polyesters or modified colophony resins and ester gums, polymers such as polyethylene, polystyrene and copolymers of styrene, polyvinyl acetate and copolymers of vinyl acetate, polyvinyl acetals of formaldehyde, acetaldehyde or butyraldehyde, polyacrylic acid esters and polymethacrylic acid esters, coumarine-indene resins, epoxy resins and polycondensates such as glycerol-phthalate resins and other glyceryl polyesters, alkyd resins, diethylene glycol polyesters, formaldehyde resins and silicone resins.

Preferred binding agents are halogen-containing polymers and epoxy resins combined with silicone resins. The sensitization of organic photoconductors with halogen-containing polymers is described in the United Kingdom Pat. No. 964,878 filed May 3, 1960 by Gevaert Photo-Producten N.V. According to said specification a material suitable for use in electrophotography comprises a photoconductive layer incorporating an organic monomeric photoconductor and a halogencontaining polymer in such layer or in a juxtaposed layer (if any), the sensitivity of said photoconductor having been increased by making it to interact with said halogen-containing polymer by heating.

In the following Table III a list of preferred polymeric binding agents is given, which may be used in combination with the heterocyclic organic photoconductors of use according to the present invention as well as the corresponding suitable solvents.

Table III

| Polymeric binding agent defined by its structural unit (s) | Solvent |
|---|---|
| 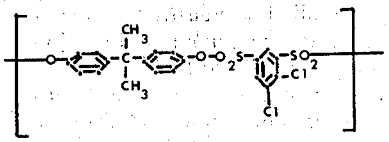 | methylene chloride |
| 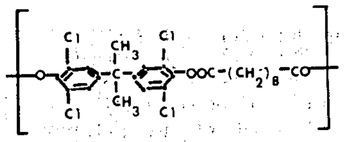 | methylene chloride |
| 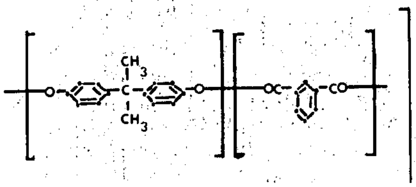 | |

Table III—Continued

| Polymeric binding agent defined by its structural unit (s) | Solvent |
| --- | --- |
| 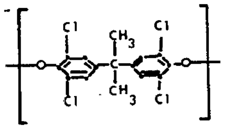 | methylene chloride |
| $-[-O-(CH_2)_6-OOC-(CH_2)_8-CO-]-$ | methylene chloride |
| 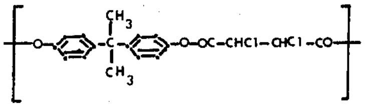 | methylene chloride |
| 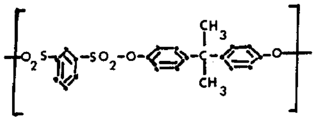 | methylene chloride |
| 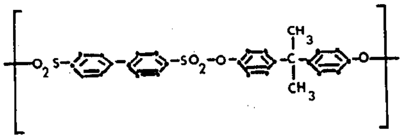 | methylene chloride |
| 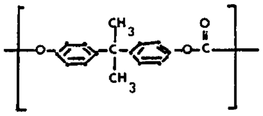 | methylene chloride |
| 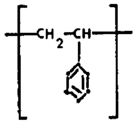 | methylene chloride |
| 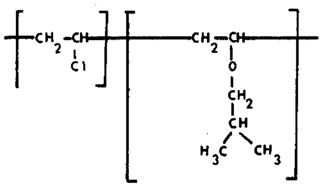 25 % by weight | methylene chloride |
| 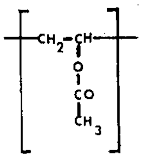 | methylene chloride |
| 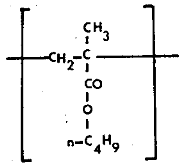 | methylene chloride |
| 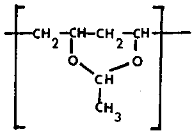 | methylene chloride |
| 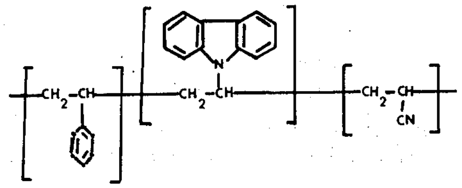 10 % by weight; 80 % by weight; 10 % by weight | methylene chloride |
| 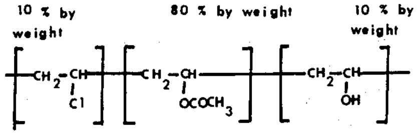 91 % by weight; 3 % by weight; 6 % by weight | methylene chloride /acetone (1:1) |

According to a special embodiment the photoconductive compounds applied according to the present invention are used in admixture with inorganic and organic photoconductive substances known to those skilled in the art, e.g. sulphur, selenium, photoconductive oxides, sulphides, and selenides of zinc, cadmium, mercury, antimony, bismuth, lead, anthracene, anthraquinone, and photoconductive polymers e.g. those containing N-vinylcarbazole recurring units and other known monomeric and polymeric organic photoconductors, e.g. those described in the published Dutch patent application Ser. No. 70/04174 filed Mar. 24, 1970 by GevaertAgfa N.V.

The inherent spectral sensitivity of most of the photoconductive compounds listed in Tables I and II is mainly situated in the near U.V. range, i.e. in the range of 360to 420 nm.

The spectral sensitivity of recording materials according to the present invention can be increased in different ways, e.g. by adding so-called spectral sensitizing agents for the photoconductive substances contained in the recording element or by admixing to the said heterocyclic organic photoconductive compounds other photoconductive substances, whose inherent sensitivity for a particular part of the electromagnetic radiation spectrum is higher than that of the present compounds.

Suitable spectral sensitizing dyestuffs for the organic photoconductor are among others organic dyestuffs, known as methine dyes, or xanthene dyes of which the phthaleins and rhodamines are subclasses, and triarylmethane dyes e.g. crystal violet (C.I. 42,555) and the triarylmethane dyes described in published Dutch patent application No. 6704706 filed Apr. 3, 1967 by Gevaert-Agfa N.V. The term methine dyes includes mono- as well as polymethine dyes, which dyes are known to those skilled in the art of the spectral sensitization of light-sensitive silver halide. Preferred methine dyes are of the cationic type. As preferred xanthene dyes Rhodamine B (C.I. 45,170), Rose Bengale (C.I. 45,440) and Fluorescein (C.I. 45,350) are mentioned. The spectral sensitizing dyes are preferably added to the recording layer composition in a proportion of 0.01 to 5% by weight in respect of the photoconductive substance(s).

Particularly preferred methine dyes are within the scope of the following general formulae:

I.

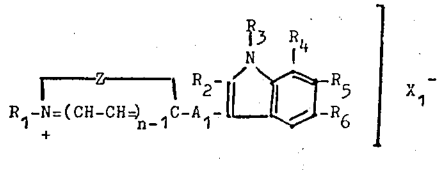

wherein:

$A_1$ stands for a dimethine or tetramethine group including a substituted dimethine or tetramethine group,

*n* stands for 1 or 2, $R_1$ stands for alkyl including substituted alkyl, an unsaturated aliphatic group e.g. allyl, aralkyl including substituted aralkyl, aryl including substituted aryl or cycloalkyl, $R_2$ stands for alkyl, aryl including substituted aryl, e.g. phenyl and phenyl substituted preferably in the p-position by alkyl, halogen and alkoxy, a 5- or 6-membered heterocycle whose heteroatom is oxygen, sulphur, selenium or nitrogen such as 2-, 3-, or 4-pyridyl, 2-furyl, 2-thienyl, etc. including their quaternary salts, $R_3$ stands for hydrogen or has one of the significances given for $R_1$, $R_4$ stands for hydrogen, alkyl, alkoxy or halogen or together with $R_3$ forms an alkylene bridge such as dimethylene and trimethylene, each of $R_5$ and $R_6$ (the same or different) stands for hydrogen, alkyl, alkoxy or halogen or together represent the atoms necessary to complete a fused-on benzene nucleus, $X_1^-$ represents an anion e.g. $Cl^-$, $Br^-$, $I^-$, $ClO_4^-$, $CH_3SO_4^-$, or

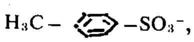, but is missing when the $R_1$ group contains already an anion (betaine type salt), and Z represents the atoms necessary to complete a heterocyclic nucleus of the types used in the production of cyanine dyes e.g. such as those of the thiazole series, e.g., thiazole, 4-methylthiazole, 4-methyl-5-carbethoxythiazole, 4-phenylthiazole, 5-methylthiazole, 5-phenylthiazole, 4-(p-tolyl)-thiazole, 4-(p-bromophenyl)-thiazole, 4,5-dimethylthiazole, 4,5-diphenylthiazole, 4-(2-thienyl)-thiazole, 4-(m-nitrophenyl)-thiazole, those of the benzothiazole series, e.g. benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 6-sulphobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, 4,5,6,7-tetrahydrobenzothiazole, 5,6-dimethoxybenzothiazole, 5,6-dioxymethylenebenzothiazole, 5-hydroxybenzothiazole, 6-hydroxybenzothiazole, 5,6-dimethylbenzothiazole, those of the naphthothiazole series e.g. naphtho[2,1-d]thiazole, naphtho[1,2-d]thiazole, 5-methoxynaphtho[1,2-d]-thiazole, 5-ethoxynaphtho[1,2-d]-thiazole, 3-methoxynaphtho[2,1-d]-thiazole, 7-methoxynaphtho[2,1-d]-thiazole, those of the thionaphtheno[ 7,6-d]-thiazole series e.g. 7-methoxythionaphtheno[7,6-d]-thiazole, those of the thiadiazole series e.g. 4-phenylthiadiazole, those of the oxazole series e.g. 4-methyloxazole, 5-methyloxazole, 4-phenyloxazole, 4,5-diphenyloxazole, 4-ethyloxazole, 4,5-dimethyloxazole, 5-phenyloxazole, those of the benzoxazole series e.g. benzoxazole, 5-chlorobenzoxazole, 5-methylbenzoxazole, 5-phenylbenzoxazole, 6-methylbenzoxazole, 5,6-dimethylbenzoxazole, 4,6-dimethylbenzoxazole, 5-methoxybenzoxazole, 6-methoxybenzoxazole, 5-hydroxybenzoxazole, 6-hydroxybenzoxazole, those of the naphthoxazole series, e.g. naphtho[2,1-d]oxazole, naphtho[1,2-d]oxazole, those of the selenazole series e.g. 4-methylselenazole, 4-phenylselenazole, those of the benzoselenazole series e.g. benzoselenazole, 5-chlorobenzoselenazole, 5-methoxybenzoselenazole, 5-methyl-6-methoxybenzoselenazole, 5,6-dioxymethylenebenzoselenazole, 5-hydroxybenzoselenazole, 4,5,6,7-tetrahydrobenzoselenazole, those of the naphthoselenazole series e.g. naphtho[2,1-d]selenazole, naphtho[1,2-d]selenazole, those of the thiazoline series e.g. thiazoline, 4-methylthiazoline, 4-hydroxymethyl-4-methylthiazoline, 4,6-bis-hydroxymethylthiazoline, those of the oxazoline series e.g. oxazoline, those of the selenazoline series e.g. selenazoline, those of the 2-quinoline series e.g. quinoline, 3-methylquinoline, 5-methylquinoline, 7-methylquinoline, 8-methylquinoline, 6-chloroquinoline, 8-chloroquinoline, 6-methoxyquinoline, 6-ethoxyquinoline, 6-hydroxyquinoline, 8-hydroxyquinoline, etc., those of the 4-quinoline series e.g. quinoline, 6-methoxyquinoline, 7-methylquinoline, 8-methylquinoline, those of the 1-isoquinoline series e.g. 1-isoquinoline, 3,4-dihydroisoquinoline, those of the 3-isoquinoline series e.g. 3-isoquinoline, those of the pyrimidine series, those of the quinoxaline series, those of the quinazoline series, those of the 1-phthalazine series, those of the 2-pyridine series, e.g. pyridine, 5-methylpyridine, 3-nitropyridine, those of the 3,3-dialkylindolenine series, e.g. 3,3-dimethylindolenine, 3,3,5-trimethylinodolenine, 3,3,7-trimethylinodolenine, etc., those of the benzimidazole series e.g. benzimidazole, 5,6-dichlorobenzimidazole, 5-chlorobenzimidazole, 5,6-dibromobenzimidazole, 5-chloro-6-amino-benzimidazole, 5-chloro-6-bromobenzimidazole, 5-phenylbenzimidazole, 5-fluorobenzimidazole, 5,6-difluorobenzimidazole, 5-cyanobenzimidazole, 5,6-dicyanobenzimidazole, 5-chloro-6-cyanobenzimidazole, 5-fluoro-6-cyanobenzimidazole, 5-acetylbenzimidazole, 5-chloro-6-fluorobenzimidazole, 5-carboxybenzimidazole, 7-carboxybenzimidazole, 5-carbethoxybenzimidazole, 7-carbethoxybenzimidazole, 5-sulphamylbenzimidazole, or 5-N-ethylsulphamylbenzimidazole, 5-ethylsulphonylbenzimidazole and 5-trifluoromethylsulphonylbenzimidazole;

II. 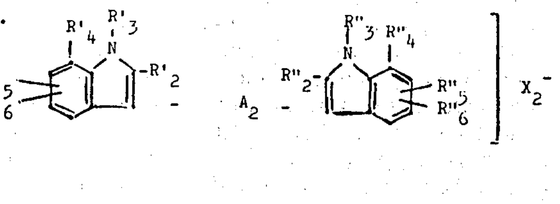

wherein:

$A_2$ stands for a monomethine or trimethine group including a substituted monomethine or trimethine group, each of $R'_2$–$R'_6$ and $R''_2$–$R''_6$ (the same or different) has one of the significances given for $R_2$–$R_6$, $X_2^-$ has the same significance as $X_1^-$;

III. 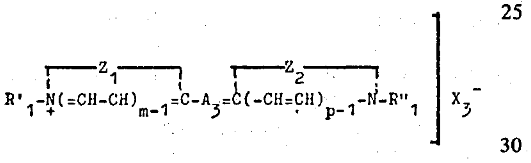

wherein:

each of $R'_1$ and $R''_1$ (the same or different) has one of the meanings given for $R_1$, $X_3^-$ has the same meaning as $X_1^-$, $A_3$ has the same meaning as $A_2$, each of *m* and *p* (the same or different) stands for 1 or 2, and each of $Z_1$ and $Z_2$ (the same or different) stands for the atoms necessary to complete a heterocyclic nucleus of the thiazole, benzothiazole, naphthothiazole, thionaphtheno[7,6-d]-thiazole, thiadiazole, oxazole, benzoxazole, naphthoxazole, selenazole, benzoselenazole, naphthoselenazole, 2-quinoline, 4-quinoline, pyrimidine, quinoxaline, quinazoline, 2-pyridine, 3,3-dialkylindolenine or of the benzimidazole series; representative examples of these heterocyclic nuclei can be found above in the definition of Z in formula I.

The dyestuffs corresponding to the above general formulae can be prepared according to the methods known by those skilled in the art of methine dye chemistry.

According to a further embodiment of the invention the recording material contains one or more substances that increase the photoconductivity of the recording material in the inherent spectral sensitivity range of the said heterocyclic organic photoconductive compounds. As already has been said a binding agent can act as a sensitizing agent that enhances the total sensitivity of the recording element. In that respect are to be mentioned compounds containing one or more electron-attracting atoms or groups, e.g. those that are known as non-ionic Lewis acids, e.g. the Lewis acids that can form a "charge transfer complex" as described e.g. in the U.S. Pat. No. 3,408,183 of Joseph Mammino issued Oct. 29, 1968. Good sensitizing results are obtained with organic carboxylic acid anhydrides and with quinones containing electron-attracting substituents, e.g. halogen or cyano, such as in tetrachlorobenzoquinone and tetracyanobenzoquinone, with organic compounds containing a

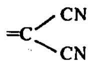

group and with the compounds according to the structural formula of the Belgian Pat. No. 734,141 filed June 6, 1969 by Gevaert-Agfa N.V. and the chlorine- and/or cyano-containing polymers of Table III.

The 1,2,3,4-tetrahydroquinoline derivatives may be used in admixture with diazonium salts that on exposure to electromagnetic radiation produce (a) radical(s) which irreversibly increase(s) the electro-conductivity of a recording layer. Such substances as well as details about their incorporation into a recording layer containing an organic photoconductive insulating substance are described in the United Kingdom Pat. No. 964,872 filed Apr. 22, 1959 by Gevaert Photo-Producten N.V. and the U.S. Pat. No. 3,113,022 of Paul Maria Cassiers, Jean Marie Nys, Jozef Frans Willems and Rene Maurice Hart issued Dec. 3, 1963. A particularly suitable conductivity-increasing diazonium compound is p-nitrobenzene-diazonium chloride. The diazonium compounds are preferably used in an amount of 0.01% to 10% by weight in respect of the present photoconductive heterocyclic organic compounds.

Other additives well known in the art of preparing photoconductive conductive coatings for recording purposes may be used, e.g. matting agents, fluorescing compounds, phosphors, optical brightening agents, agents controlling the adhesive power of the recording layer, agents controlling the elasticity, the plasticity and the hardness of the recording layer, agents controlling the viscosity of the coating composition, antioxidants, gloss-improving agents, etc.

Transparent and semi-transparent recording materials containing the photoconductive heterocyclic organic compounds as described hereinbefore are especially suited for use in recording materials applied for the production and reproduction of microfilm images. Microfilm images can be copied in contact or enlarged optically on recording materials according to the present invention. According to the type of development, the transparencies obtained (contact copies and enlargements) can serve as negative or positive intermediate prints for further printing, e.g. on diazotype materials.

The semitransparent recording materials according to the present invention preferably have an optical density not larger than 0.30 towards visible light or the copying light used in the printing apparatus wherein it is used as intermediate print.

The photoconductive heterocyclic organic compounds described hereinbefore are further especially suited for being applied in the manufacture of pigment images wherein the pigments may have the properties of a fluorescent compound or phosphor.

As is generally known luminescent phosphors are used in screens of cathode-ray tubes and more particularly in television, X-ray, radar and oscilloscope screens. It is further known that in color television screens phosphors of different color have to be fixed on a screen in a particular pattern.

The described photoconductive compounds are successfully used in a process for the production of color television screens as described in the French Pat. No. 1,336,499 filed Sept. 26, 1962 by Comp. Francaise Thomson-Houston. According to the process described in said specification a pattern of a phosphor on a screen support is produced by the steps of applying to said support a coating of an electroconductive material and to said coating a layer comprising a vaporisable or thermolysable photoconductive compound optionally incorporated in a vaporisable or thermolysable binding agent. On said coating an electrostatic charge pattern corresponding with the pigment pattern to be produced is formed in an electrophotographic way, and the electrostatic charge pattern is developed with non-volatile powder particles that have the desired phosphorescent or luminescent properties. Subsequently the photoconductive layer containing the phosphor powder image is heated in order to remove the volatile substances of the photoconductive recording layer and to make the phosphor pattern adhere to the screen support.

In order to fix the powder image before applying the heating step it is preferably overcoated with a layer of a thermolysable binding agent.

According to said French patent photoconductors of the group of anthracene, anthraquinone and xanthene are used. The recording layer may further contain boric acid.

The photoconductors mentioned in the French patent are advantageously partly or wholly substituted by the photoconductive substances applied according to the present invention.

Suitable thermolysable binding agents belong to the class of the polyacrylic acid esters and polymethacrylic acid esters, e.g. polymethyl methacrylate, polyethyl methacrylate and polyethyl acrylate.

The thickness of the photoconductive layers of the present invention is not critical but is open to choice within a wide range according to requirements in each individual case. Good results are attained with photoconductive layers of a thickness between 1 and 30 $\mu$ preferably between 3 and 20 $\mu$. Too thin layers do not have a sufficient insulating power in the absence of active electromagnetic radiation, whereas too thick layers require extensive exposure times. The photoconductor may be used in a self-supporting or supported layer.

In the manufacture of electrophotographic recording materials according to the present invention preferably a relatively conductive support for the recording layer is used, e.g. an electroconductive sheet or plate, or an insulating sheet or plate covered with an electro-conductive interlayer. By electro-conductive plate or sheet is understood a plate or sheet whose electrical resistivity is smaller than that of the non-irradiated (dark-adapted) photoconductive layer i.e. in general smaller than $10^9$ ohm.cm and preferably is at least 100 times as small as that of the recording layer. Supports whose resistivity is not higher than $10^7$ ohm.cm are preferred. The recording layers themselves have preferably an electrical insulating power as high as possible without affecting too much the photosensitivity by means of too high an amount of insulating binding agent. Preferably the recording layers have in non-irradiated state (dark-adapted state) a resistivity of at least $10^9$ ohm.cm.

Suitable conductive plates are, e.g., plates of metals such as aluminium, zinc, copper, tin, iron, or lead.

Suitable electro-conductive interlayers for insulating supports are, e.g., vacuum-coated metal and conductive metal compound (metal oxide or metal salt) layers such as silver, tin, aluminium, titanium dioxide and copper iodide conductive layers, transparent conductive polymer layers, e.g. applied from polymers containing quaternized nitrogen atoms, such as those described in the United Kingdom Pat. No. 950,960 filed Sept. 23, 1960 by Gevaert Photo-Producten N.V., or layers containing conductive particles, e.g. carbon black and metal particles dispersed in a binder. The binder used for said particles has a resistivity preferably lower than $10^6$ ohm.cm. A suitable binder for that purpose is gelatin.

It is possible to produce transparent photoconductive recording materials by applying the photoconductive compounds together with a suitable binder (if necessary) from a clear solution to a conductive transparent base or a transparent insulating base coated with an electroconductive transparent interlayer.

As transparent bases resin sheets having an optical density of not more than 0.10 are preferred, e.g., a sheet made of polyethylene terephthalate or cellulose triacetate. The conductive interlayer preferably consists of a metal coating. e.g., a vacuumcoated aluminium layer having an optical density of not more than 0.30, or of a conductive transparent polymer layer composed, e.g., of an organic polyionic polymer, e.g. a polymer containing quaternized nitrogen atoms such as a quaternized polyethylene-imine.

In reproduction techniques wherein the prints are to be produced on an opaque background preferably a paper sheet is used as support for the recording layer.

Paper sheets that have an insufficient electrical conductivity are coated or impregnated with substances enhancing their conductivity, e.g. by means of a conductive overcoat such as a metal sheet laminated thereto.

As substances suited for enhancing the conductivity of a paper sheet and which can be applied in the paper mass are particularly mentioned hygroscopic compounds and antistatic agents as described, e.g., in the United Kingdom Pat. No. 964,877 filed May 2, 1960 by Gevaert Photo-Producten N.V., and antistatic agents of polyionic type, e.g. CALGON CONDUCTIVE POLYMER 261 (trade mark of Calgon Corporation, Inc. Pittsburgh, Pa., U.S.A.) for a solution containing 39.1% by weight of active conductive solids, which contain a conductive polymer having recurring units of the following type:

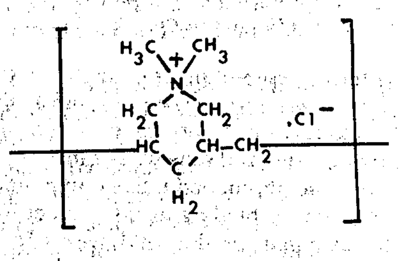

Paper sheets are preferably impermeabilized to organic solvents, e.g. by means of a water-soluble colloid or by strongly hydrating the cellulose fibers such as in the case of glassine paper.

In order to prepare an electrophotographic material according to the present invention various techniques may be applied.

In practice, the photoconductive substances involved, either alone or together with other additives such as those described above, preferably are first dissolved or dispersed in a suitable organic solvent such as a chlorinated hydrocarbon, e.g. methylene chloride. The solution or dispersion thus obtained is uniformly spread on a surface of a suitable support, e.g. by centrifuging, spraying, brushing, or coating. Thereupon the layer formed is dried in such a way that a solid photoconductive layer is formed on the surface of the support.

Recording materials according to the present invention can be used in any of the different techniques known in recording with the aid of photoconductors. According to a preferred embodiment they are used in a technique based on the discharge of an electrostatically charged recording layer by exposure to light.

Photoconductive recording materials prepared according to the present invention can be used in exposure units equipped with incandescent lamps, so that they need not be exposed with light rays rich in ultraviolet such as those emitted by a high-pressure mercury vapour bulb.

The electrostatic charging of photoconductive recording elements according to the present invention can be effected according to any method known in electrophotography, e.g. by friction with a smooth material, with a material possessing a high electric resistance, e.g. a cylinder coated with polystyrene, by corona discharge, by contact charge, or by discharge of a capacitor.

Recording materials containing the said organic photoconductive substances can be used in a recording technique comprising a negative corona charging as well as in a recording technique comprising a positive corona charging.

In order to obtain an electrostatic image it is possible to effect the charging and exposure steps simultaneously and even to expose the recording layer image-wise before charging since a conductivity image is formed that is not destroyed immediately, especially if diazonium salts are used in the recording element. It is preferred, however, that the charging is effected before image-wise exposure.

The electrostatic latent image can be converted into a visible image either on the electrophotographic material wherein the latent image was formed, or on a material to which the electrostatic latent image was transferred, e.g. by application of the method described in the Belgian Pat. No. 529,234 filed May 29, 1954 by Chester Floyd Carlson.

The conversion of the original or transferred latent image into a visible image can occur according to one of the techniques known in electrophotography, wherein use is made of a conductivity pattern (e.g. electrolysis) or the electrostatic attraction or repulsion of finely divided colored substances, which, e.g., are present in a powder mixture, in an electrically insulating liquid (e.g. in the form of a suspension) or in a gas (e.g. in the form of an aerosol), or wherein electrostatic attraction is used for selectively wetting charged portions of the recording layer, as described in the United Kingdom Pat. Nos. 1,020,505 filed Nov. 8, 1961 and 1,033,419 filed Nov. 26, 1962 both by Gevaert Photo-Producten N.V.

When the sign of the charge of the developing powder or developing liquid is properly chosen, either a negative or a positive print can be obtained from any original. If both printing material and developing powder or developing liquid have the same sign of charge, the powder only adheres to the discharged areas so that a negative print is obtained. If the signs of the recording material and of the developing powder or developing liquid differ, a positive print is obtained.

If a colored powder is used for making visible the latent image, the visible image obtained can, if necessary, be fixed according to one of the methods known in electrophotography, e.g., by heating, or it can be transferred to another support, e.g. according to the method described in the United Kingdom Pat. No. 658,699 filed Apr. 14, 1949 by Battelle Memorial Institute and fixed thereon.

The present heterocyclic organic photoconductive compounds can also be supplied in a thermoplastic recording process to form a ripple-image as described, e.g., in the United Kingdom Pat. No. 964,811 filed May 17, 1960 by Gevaert Photo-Producten N.V.

Evidently the present invention by no means is limited to one or other particular embodiment of using the electrophotographic material containing the photoconductive compounds as described herein. The exposure technique, the charging method, the formation of the charge pattern, the transfer of such pattern if applied, the developing method, and the fixation or the transfer of the developing material pattern may be modified or adapted.

The composition of the recording materials used in these methods may be adapted to the requirements of the recording process used.

Electrophotographic materials according to the present invention can be employed in reproduction techniques, wherein different kinds of electromagnetic radiations are used, e.g. visible light, U.V.-radiation, X-rays and γ-rays.

The following examples illustrate the present invention.

The percentages and ratios are by weight unless otherwise indicated.

EXAMPLE 1

An aluminium-laminated paper sheet was coated with the following composition:

| | |
|---|---|
| 10 % by weight solution in methylene chloride of an organic photoconductor listed in Table I or II | 50 ml |
| copoly(vinyl chloride/vinyl acetate/maleic anhydride) (mol ratio 86.5/13.3/0.2) | 5 g |
| 1,2-dichloro-ethane | 45 ml. |

The coating was carried out in such a ratio that the dried photoconductive layer contained 2 g of photoconductor per sq.m.

After a negative corona charging with a potential difference of −6000 V between the corona wires and the ground, the charged recording layer was contact-exposed for 30 sec through a step wedge having 0.20 log exposure increments. In this exposure 5 Osram (trade name) L 20 fluorescent tubes, mainly emitting in the U.V. range and the shorter wavelengths of the visible spectrum were placed at a distance of 20 cm from the recording layer.

The latent wedge image obtained was electrophoretically developed by means of an electrophoretic developer prepared by diluting the concentrated developer composition described hereinafter in a volume ratio of 15/1000 by means of ISOPAR H (an isoparaffinic hydrocarbon mixture having a boiling range of 177°–188°C sold by Esso Belgium N.V., Antwerp, Belgium):

| | |
|---|---|
| carbon black (average particle size : 20 nm) | 30 g |
| zinc monotridecyl phosphate as dispersing agent | 1.5 g |
| ISOPAR H (trade name) | 750 ml |
| resin solution prepared as described hereinafter | 150 g |

The resin binder solution was prepared by heating 500 g of ALKYDAL L 67 (of Farbenfabriken Bayer A.G., Leverkusen, W. Germany for a linseed oil-modified (67% by weight) alkyd resin) and 500 ml of white spirit containing 11% by weight of aromatic compounds at 60°C till a clear solution was obtained, and subsequent cooling.

A black positive copy of the wedge original on a transparent base was obtained.

From the wedge prints obtained the relative speed values of the developed materials were calculated based on a comparison of the number of non-toned (discharged) steps present in the wedge prints obtained with materials containing a photoconductor of Table I or II with the number of non-toned steps produced in a material containing photoconductor number 3 of Table II to which is given arbitrarily the speed value 100.

| Number of compound of Table I or II | Relative Speed values |
|---|---|
| 1,I | 25 |
| 2,I | 2.5 |
| 1,II | 250 |
| 2,II | 250 |
| 3,II | 100 |
| 5,II | 160 |
| 6,II | 160 |
| 7,II | 60 |

EXAMPLE 2

An electrophotographic recording material was prepared by coating onto an aluminium laminated paper a solution containing:

| | |
|---|---|
| 10% by weight solution in methylene chloride of an organic photoconductor listed in Table I or II | 50 ml |
| copoly(vinyl chloride/vinyl acetate/maleic anhydride) (mol ratio 86.5/13.3/0.2) | 5 g |
| Rhodamine B (C.I. Basic Violet 10 C.I. 45,170) | 0.025 g |
| 1,2-dichloroethane | 45 ml. |

The dried recording layer contained 2 g of photoconductor per sq.m.

The coated samples were negatively charged with a negative corona having a potential difference of −6000 V between the corona wires and the ground.

The charged recording layer was contact-exposed for 6 sec. through a step-wedge having 0.20 log exposure increments. In the exposure tungsten filament lamp light was used.

The latent wedge images were electrophoretically developed as described in Example 1.

The relative speed values of the developed materials were compared with the electrophotographic material containing photoconductor number 3 of Table II which is given arbitrarily the speed value 100.

| Number of compound of Table I or II | Relative Speed values |
|---|---|
| 1,I | 25 |
| 2,I | 1 |
| 3,I | 25 |
| 4,I | 1 |
| 6,I | 2.5 |
| 1,II | 100 |
| 2,II | 40 |
| 3,II | 100 |
| 5,II | 250 |
| 6,II | 100 |
| 7,II | 40 |

EXAMPLE 3

To a polyethylene terephthalate support of 100 μ a conductive transparent coating was applied from an aqueous solution of gelatin and CALGON CONDUCTIVE POLYMER 261 in a weight ratio of 2:1. Coating was carried out in such a way that the dried coating contained 2 g of gelatin per sq.m. The electric resistivity of the coating was $1 \times 10^6$ ohm per sq.cm.

An electrophotographic recording material was prepared by coating onto said conductive layer a solution consisting of

| | |
|---|---|
| methylene chloride | 45 ml |
| 1,2-dichloro-ethane | 45 ml |
| 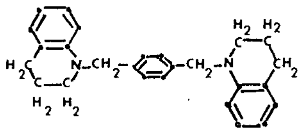 | 5 g |
| copoly(vinyl chloride/vinyl acetate/maleic anhydride)(molar ratio 86.5/13.3/0.2) | 5 g |
| Rhodamine B (C.I. Basic Violet 10; C.I. 45,170) | 0.025 g |

The dried recording layer containing approximately 3 g of photoconductor per sq.m., was charged with a negative corona and contact-exposed with 100 lux.sec with the same light source as in Example 2. The latent image was electrophoretically developed for 5 sec. with the developer described in Example 1. A good copy of the original was obtained.

EXAMPLE 4

To a polyethylene terephthalate support of 63 μ a conductive transparent coating was applied from

| | |
|---|---|
| a 10% aqueous solution of polystyrene sulphonic acid sodium salt | 40 ml |
| methanol | 60 ml. |

The coating was carried out in such a way that the dried material contained 1.75 g of polystyrene sulphonic acid sodium salt per sq.m. The electrical resistivity was $5 \times 10^6$ /cm$^2$.

An electrophotographic recording material was prepared by coating onto said conductive layer at a coverage of 3 g per sq.m of photoconductor a solution containing:

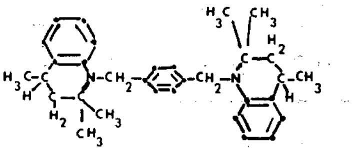

5 g

| | |
|---|---|
| copoly(vinyl chloride/vinyl acetate/maleic) anhydride)(molar ratio 86.5/13.3/0.2) | 5 g |
| methylene chloride | 45 g |
| 1,2-dichloroethane | 45 g |

After a negative corona charging with a potential difference of −6000 V, the charged recording layer was contactexposed for 30 sec through a positive transparency of a test chart with 5 Osram (trade name) L 20 fluorescent tubes at a distance of 20 cm from the recording layer.

After the exposure the latent image was developed for 5 sec with a triboelectrically charged positive toner on the base of three parts by weight of pitch, 4 parts by weight of colophony and 3 parts by weight of carbon black.

A contrasty transparent positive copy of the transparency was obtained.

EXAMPLE 5

The effect on the speed of electrophotographic recording materials resulting from a few chemical sensitizers was examined.

Therefor the following photoconductive compositions were coated on an aluminium laminated paper:

| | |
|---|---|
| 10% by weight solution in methylene chloride of the organic photoconductor number 2 of Table II | 50 ml |
| copoly(vinyl chloride/vinyl acetate/maleic anhydride)(molar ratio 86.5/13.3/0.2) | 5 g |
| a chemical sensitizer listed in Table IV | 0.05 g. |

The dried layers contained 2 g of photoconductor per sq.m.

Processing of the materials was carried out in the same way as described in Example 1. The relative speed values are listed hereinafter.

Table IV

| Test no | Structural formula chemical sensitizer | relative speed value |
|---|---|---|
| 0 | none | 100 |
| 1 | 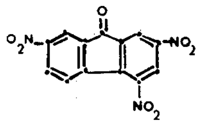 | 250 |
| 2 | 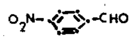 | 250 |
| 3 | 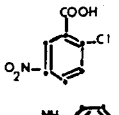 | 250 |
| 4 | 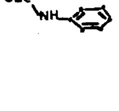 | 160 |

Table IV – Continued

| Test no. | Structural formula chemical sensitizer | relative speed value |
|---|---|---|
| 5 | 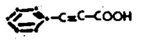 | 400 |
| 6 | 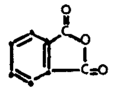 | 160 |
| 7 | 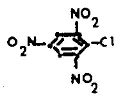 | 160 |
| 8 | 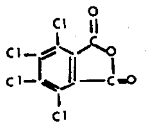 | 400 |
| 9 | 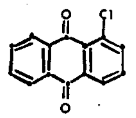 | 250 |
| 10 | 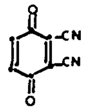 | 250 |
| 11 | 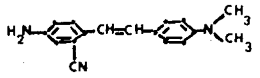 | 1600 |

EXAMPLE 6

Electrophotographic recording materials were prepared by coating onto a conductive layer as described in Example 3 a composition containing:

| | |
|---|---|
| compound number 4 of Table II | 5 g |
| copoly(vinyl chloride/vinyl acetate/maleic anhydride)(molar ratio 86.5/13.3/0.2) | 5 g |
| methylene chloride | 45 ml |
| 1.2-dichloroethane | 45 ml |
| a sensitizing dye as listed in the table V | 0.025 g |

The recording layers were charged, exposed and developed as described in Example 3.

From the obtained prints the relative speed values were calculated based on a comparison of the spectrally sensitized materials with the material without spectral sensitizer to which arbitrarily the speed value of 100 was given.

The relative speed values are listed hereinafter.

Table V

| No. | Structural formula of spectral sensiting agent | Relative speed value |
|---|---|---|
| 0 | no e | 100 |
| 1 | 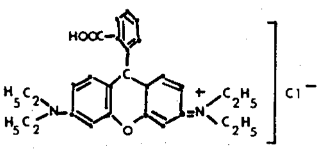 | 4000 |

Table V – Continued

| No. | Structural formula of spectral sensiting agent | Relative speed value |
|---|---|---|
| 2 | 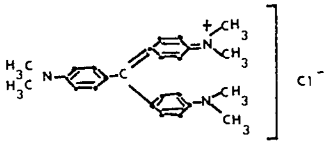 | 4000 |
| 3 | 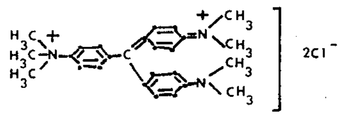 | 250 |
| 4 | 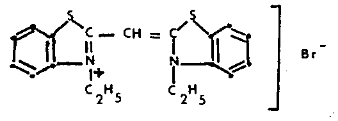 | 600 |
| 5 | 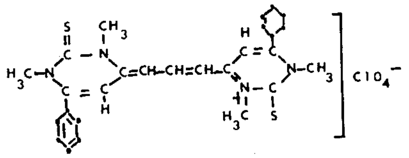 | 1600 |
| 6 | 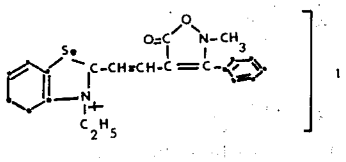 | 250 |
| 7 | 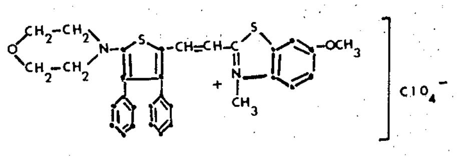 | 1600 |
| 8 | 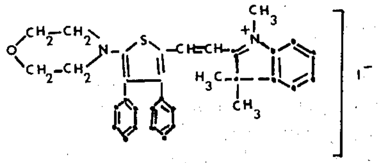 | 4000 |
| 9 | 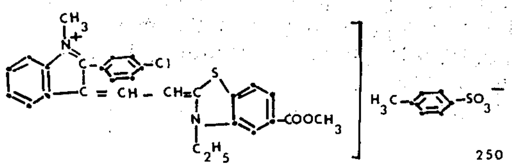 | 250 |
| 10 | 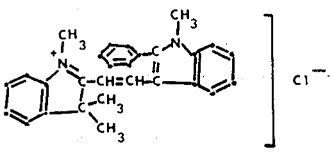 | 400 |
| 11 | 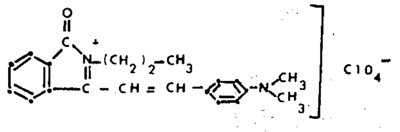 | 400 |
| 12 | 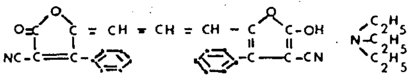 | 1600 |
| 13 | 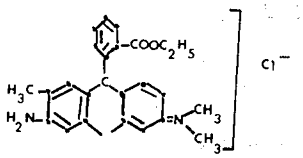 | 1600 |

EXAMPLE 7

An electrophotographic recording material was prepared by coating onto a conductive layer as described in Example 3 a solution containing:

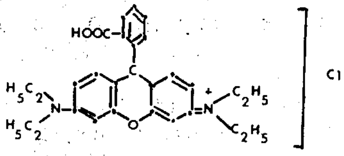

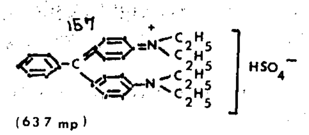

(637 mp)

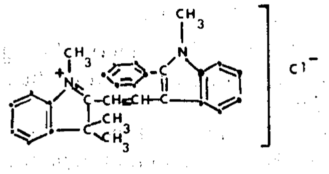

The coating was carried out at a coverage of 1.35 g of photoconductor per sq.m.

After a negative corona charging the recording layer was exposed in a microfilm camera for 10 sec. with 1,500 lux to a halftone multicolor original. The diaphragma setting was 4.5 and the original was reduced optically 20 times. The obtained electrostatic charge image was developed as described in Example 1.

We claim:

1. A chemical compound having photoconductive properties and corresponding to the formula:

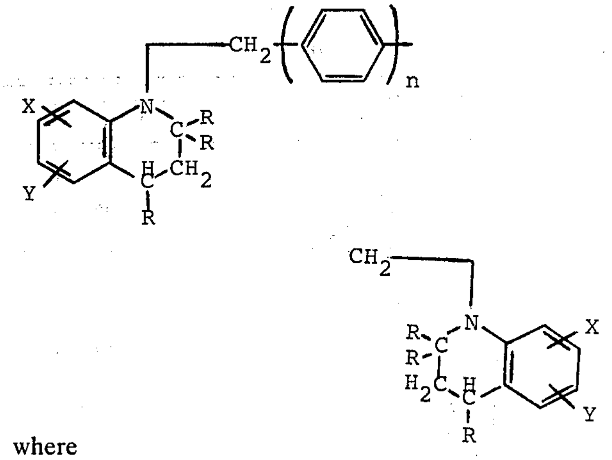

where

*n* is 1,

X and Y are hydrogen,

R is hydrogen or methyl

2. A compound according to claim 1 wherein R is a methyl group.

* * * * *